(12) United States Patent
Bao

(10) Patent No.: US 8,829,395 B2
(45) Date of Patent: Sep. 9, 2014

(54) LED TORCH

(76) Inventor: Fan Bao, City of Industry, CA (US)

( * ) Notice: Subject to any disclaimer, the term of this patent is extended or adjusted under 35 U.S.C. 154(b) by 987 days.

(21) Appl. No.: 12/925,467

(22) Filed: Oct. 21, 2010

(65) Prior Publication Data

US 2012/0097660 A1   Apr. 26, 2012

(51) Int. Cl.
*H05B 1/00* (2006.01)
*H05B 3/00* (2006.01)
*H05B 11/00* (2006.01)
*A61M 11/04* (2006.01)

(52) U.S. Cl.
CPC ...... *H05B 3/0033* (2013.01); *A61M 2205/8206* (2013.01); *A61M 11/042* (2014.02); *A61M 11/041* (2013.01); *A61M 2205/583* (2013.01); *A61M 2205/587* (2013.01); *A61M 2205/3368* (2013.01); *A61M 2205/6018* (2013.01); *A61M 2205/502* (2013.01)
USPC ........................................................ 219/209

(58) Field of Classification Search
CPC ............. H05B 3/0033; A61M 11/041; A61M 11/042; A61M 2205/502; A61M 2205/583; A61M 2205/587; A61M 2205/6018; A61M 2205/8206
USPC ......... 219/201, 209, 482, 494, 502, 505, 506, 219/533; 392/386–395, 405; 128/200.14, 128/203.14, 203.26, 204.17; 131/194, 328
See application file for complete search history.

(56) References Cited

U.S. PATENT DOCUMENTS

| | | | |
|---|---|---|---|
| 2009/0050139 A1* | 2/2009 | Watanabe et al. | 128/200.14 |
| 2009/0095287 A1* | 4/2009 | Emarlou | 128/200.14 |

\* cited by examiner

*Primary Examiner* — Dana Ross
*Assistant Examiner* — Lindsey C Teaters
(74) *Attorney, Agent, or Firm* — Raymond Y. Chan; David and Raymond Patent Firm

(57) ABSTRACT

A LED torch includes a hand-held housing, an electrical power arrangement, and a multifunctional head unit. The electric power arrangement includes an electric power source and an electrical-powered operation head electrically linked to the electric power source. The multifunctional head unit includes an inhaler unit and a LED illumination unit detachably and interchangeably coupled with the hand-held housing to operatively link to the operation head. When the inhaler unit is operatively coupled with the operation head, the operation head forms a heating head for heating the treatment element in the treatment cavity to extract the treatment element for inhalation of an ingredient thereof via the mouthpiece. When the LED illumination unit is operatively coupled with the operation head, the operation head forms an electrical adapter to electrically link the LED illumination unit with the electric power source for generating illumination light.

17 Claims, 5 Drawing Sheets

LED TORCH

BACKGROUND OF THE PRESENT INVENTION

1. Field of Invention

The present invention relates to a vaporizer, and more particular to a LED torch, which is a portable herbal and aromatherapy vaporizer for heating up a treatment element by means of electrical power to extract for inhalation of the ingredient of the treatment element.

2. Description of Related Arts

A vaporizer is a device commonly used for releasing medicinal or psychoactive compounds from plant materials, such as Lavender. For medical or recreational purpose, vaporizing is an alternative to smoking. Rather than burning, a vaporizer heats the plant material to around 200° C. so that the volatile psychoactive and medicinal constituents contained in the plant melt and phase into an aromatic vapor that does not contain the particular matter, such as tars, found in the smoke.

A portable vaporizer is provided with a compact size for enabling the user to carry the vaporizer. Generally speaking, the existing portable vaporizer comprises a hand-held housing containing a fuel chamber, a fuel-powered piezoelectric igniter operatively linked to the fuel chamber, and a mouthpiece holding the substance. Accordingly, once the fuel chamber is filled with combustible fuel, such as butane gas, the piezoelectric igniter is ignited when the combustible fuel is released from the fuel chamber. In other words, the piezoelectric igniter is actuated, the substance will be heated up and extracted for inhalation of the ingredient of the substance via the mouthpiece. However, the existing portable vaporizer has several drawbacks.

The portable vaporizer must be filled by combustible fuel which is highly flammable. In other words, it is unsafe for the user to carry the relatively high amount of combustible fuel. In addition, it is a hassle for the user to refill the combustible fuel once the fuel chamber is empty or near empty. However, the user always has a hard time to find the combustible fuel anywhere for refilling purpose. Otherwise, the user must carry an additional bottle of combustible fuel for refilling the vaporizer in case that the combustible fuel of the vaporizer is used up.

It is appreciated that the volume of the fuel chamber can be increased in order to contain relatively more combustible fuel therein for prolonging the service span of the vaporizer. However, the overall size of the hand-held housing must be corresponding increased to fit the fuel chamber in the hand-held housing. Therefore, the portability of the vaporizer will be substantially reduced. In other words, the vaporizer can be reduced its size to enhance the portability thereof. But, the size of the fuel chamber will be compensated to reduce the volume of combustible fuel therein.

The substance is heated by the vaporizer via the piezoelectric igniter. As to heating, the substance is placed on a metal plate or a hot surface which is heated to release the active constituents. However, the heating temperature of the piezoelectric igniter is hard to be controlled through the combustible fuel, especially to control the heating temperature at a constant temperature. If the heating temperature is too low, the substance cannot be extracted effectively. If the heating temperature is too high, the substance may be burned as a result.

During the operation of the vaporizer, there is always a residual gas remaining in the vaporizer even though the gas valve of the fuel chamber is shut off. Due to the structural configuration of the vaporizer, the residual gas must be gradually released through the piezoelectric igniter. Since the residual gas is highly flammable, the residual gas will be easily burn or ignited, causing fire or combustion. It is worth mentioning that the gas valve and a safety valve must be incorporated with the fuel chamber to control the release of the combustible fuel. Therefore, the manufacturing cost of the vaporizer will be substantially increased by additional components including the gas valve and the safety valve.

In addition, the user will always smell the combustible fuel during the operation of the vaporizer. Even though the vaporizer is switched off, the user will keep inhaling the residual gas for a period of time. It is known that the combustible fuel is unhealthy when it is inhaled.

As it is mentioned above, the safety valve must be incorporated with the fuel chamber for preventing the leakage of the combustible fuel. However, once the safety valve is malfunctioned, the combustible fuel may be accidentally leaked out of the fuel chamber by any unintentional operation such as accidentally pressing the operation button of the vaporizer.

Furthermore, since the vaporizer is powered by combustible fuel, the vaporizer can only provide a single function of inhaling the substance. In other words, the user must carry the vaporizer everywhere for only inhalation of the ingredient of the substance without any other additional function.

SUMMARY OF THE PRESENT INVENTION

The invention is advantageous in that it provides a LED torch, which is a portable herbal and aromatherapy vaporizer for heating up a treatment element by means of electrical power to extract for inhalation of the ingredient of the treatment element.

Another advantage of the invention is to provide a LED torch, wherein no combustible fuel is used in order to heat up the treatment element so as to provide a safe and convenient way for the user to operate the LED torch.

Another advantage of the invention is to provide a LED torch, which comprises an electric-powered heating element operatively linked to an electric power source such that the heating element will heat up the treatment element by closing the electric circuit between the heating element and the electric power source.

Another advantage of the invention is to provide a LED torch, wherein the user is able to replace the electric power source as the replaceable battery or recharge the electric power source as the rechargeable battery to prolong the service life span of the LED torch instead of refilling the combustible fuel to the conventional vaporizer.

Another advantage of the invention is to provide a LED torch, wherein the mouthpiece and the LED light unit are interchangeable to selectively connect to the electric power source. Therefore, the LED torch of the present invention provides multiple functions of inhaling purpose and illumination purpose.

Additional advantages and features of the invention will become apparent from the description which follows, and may be realized by means of the instrumentalities and combinations particular point out in the appended claims.

According to the present invention, the foregoing and other objects and advantages are attained by a LED torch which comprises a hand-held housing, an electrical power arrangement, and a multifunctional head unit.

The electric power arrangement comprises an electric power source received in the hand-held housing and an electrical-powered operation head which is electrically linked to the electric power source and is located at an outer wall of the hand-held housing.

The multifunctional head unit comprises an inhaler unit and a LED illumination unit detachably and interchangeably coupled with the hand-held housing to operatively link to the operation head, wherein the inhaler unit has a mouthpiece and a treatment cavity for receiving a treatment element therein. When the inhaler unit is operatively coupled with the operation head of the electric power arrangement, the operation head forms a heating head for heating the treatment element in the treatment cavity so as to extract the treatment element for inhalation of an ingredient thereof via the mouthpiece. When the LED illumination unit is operatively coupled with the operation head of the electric power arrangement, the operation head forms an electrical adapter to electrically link the LED illumination unit with the electric power source for generating illumination light.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
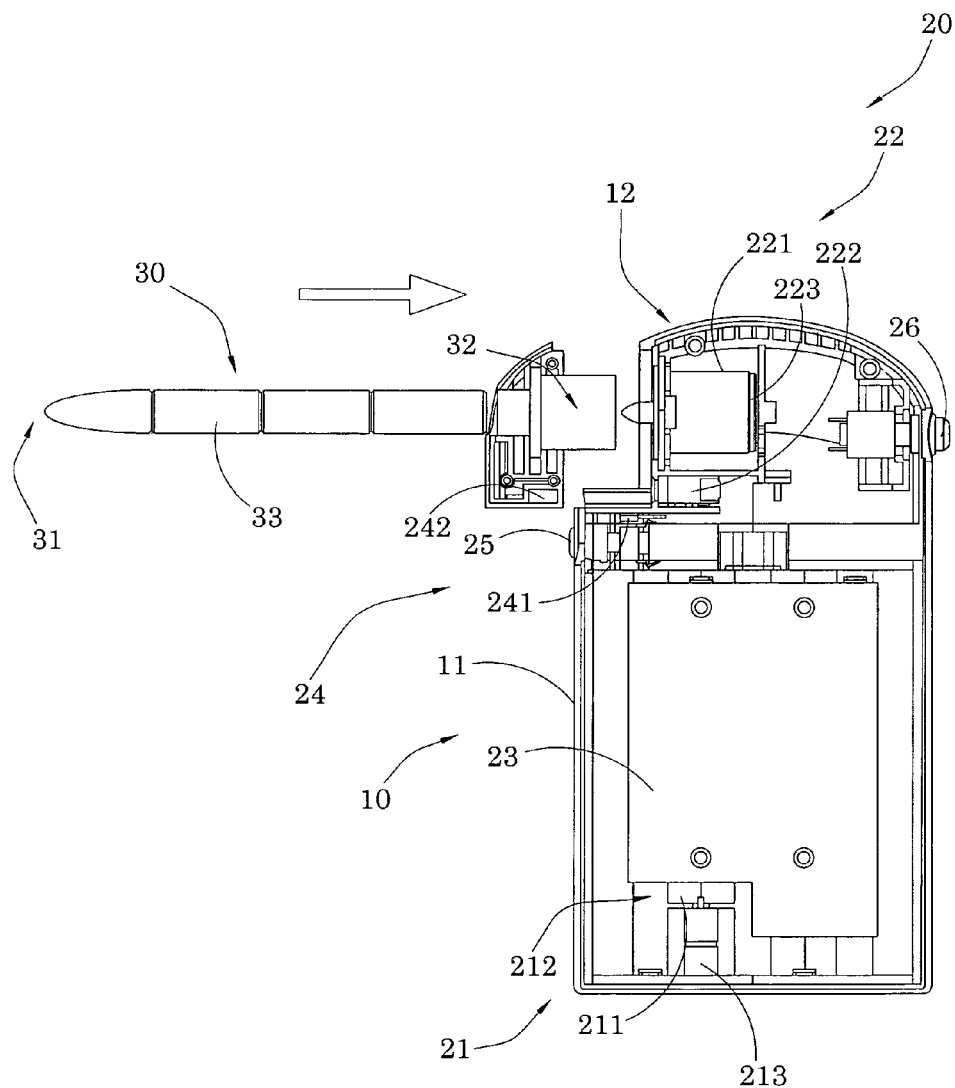
FIG. 1 is a sectional view of a LED torch according to a preferred embodiment of the present invention, illustrating an inhaler unit being detachably coupled with the hand-held housing.
Figure 2:
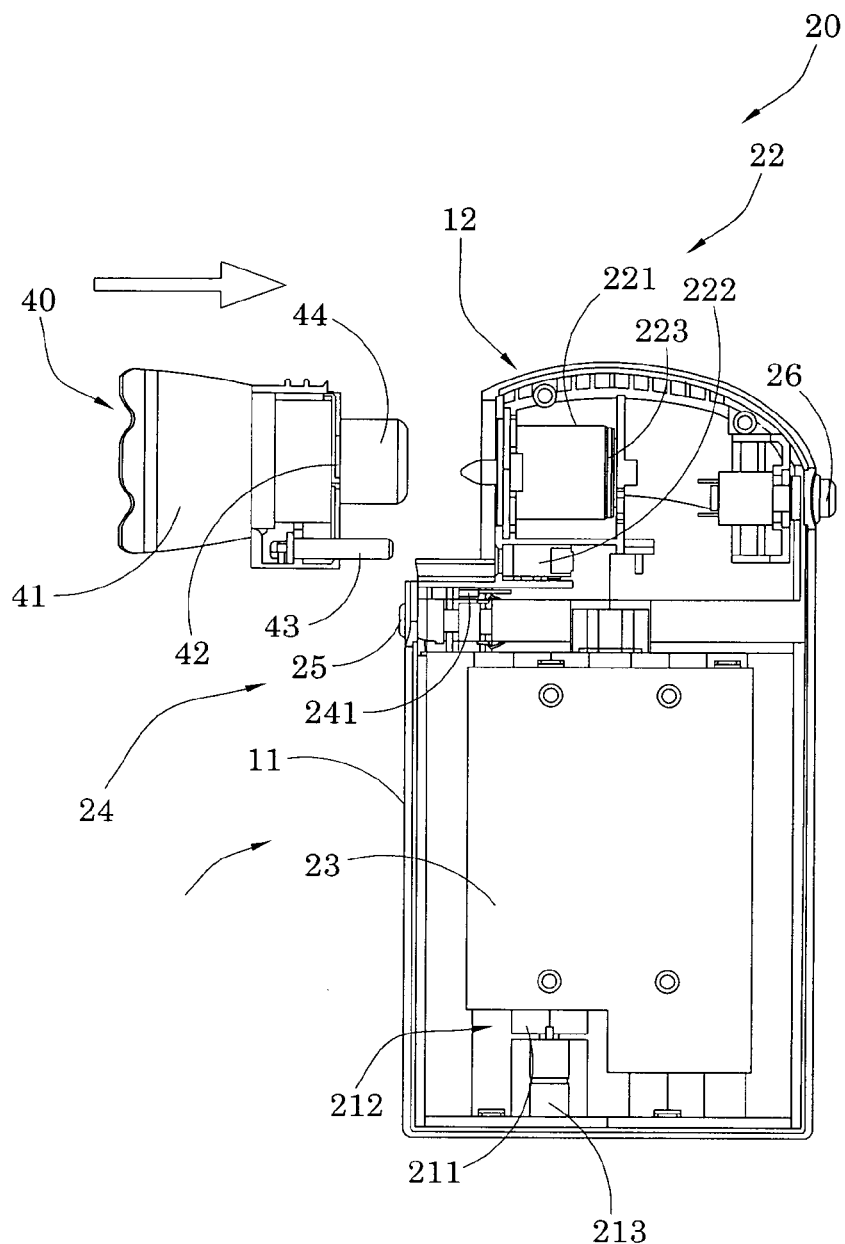
FIG. 2 is a sectional view of the LED torch according to the above preferred embodiment of the present invention, illustrating a LED illumination being detachably coupled with the hand-held housing.

Referring to FIGS. 1 and 2 of the drawings, a LED torch according to a preferred embodiment of the present invention is illustrated, wherein the LED torch, which is embodied as a portable herbal and aromatherapy vaporizer, comprises a hand-held housing 10, an electrical power arrangement 20, and a multifunctional head unit.

Figure 3:
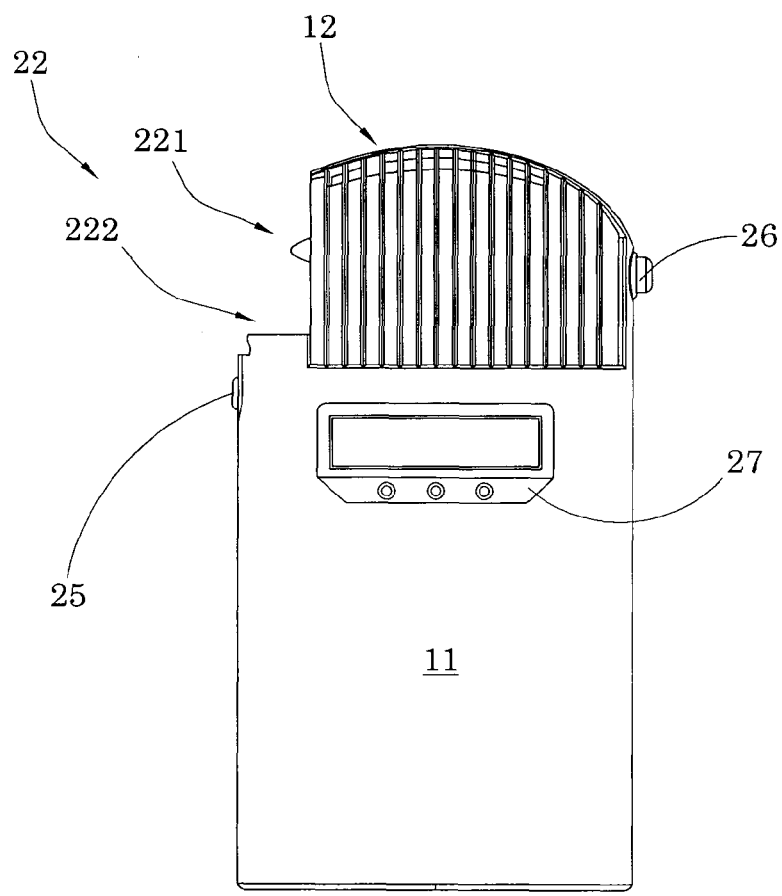
FIG. 3 is a side view of the hand-held housing of the LED torch according to the above preferred embodiment of the present invention.
Figure 4:
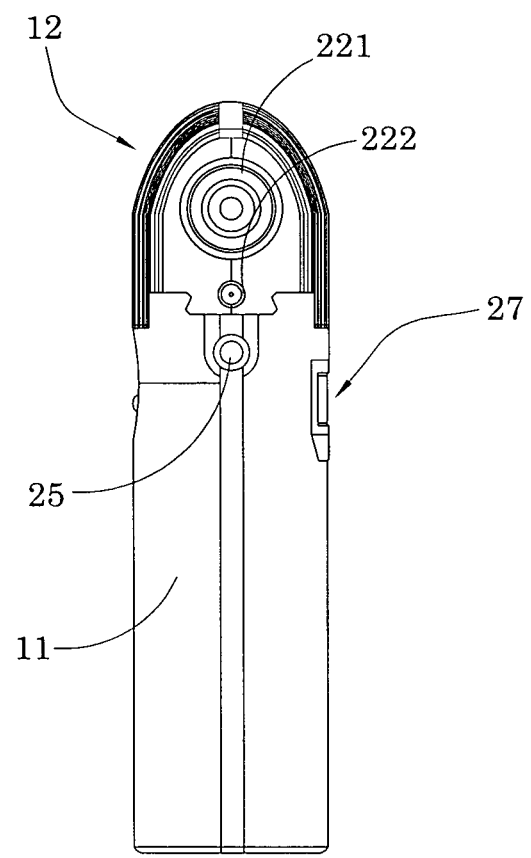
FIG. 4 is a front view of the hand-held housing of the LED torch according to the above preferred embodiment of the present invention.

As shown in FIGS. 3 and 4, the hand-held housing 10 has a hand size adapted for being held of the hand of the user, wherein the hand-held housing 10 has an outer wall 11 defining a top face, a bottom face, two side faces, a front face, and a rear face.

The electric power arrangement 20 comprises an electric power source 21 received in the hand-held housing 10 and an electrical-powered operation head 22 which is electrically linked to the electric power source 21 and is located at the outer wall 11 of the hand-held housing 10. In particular, the operation head 22 is located at the front face of the hand-held housing 10 at the upper portion thereof.

The multifunctional head unit comprises a plurality of functional units being interchangeably coupled with the hand-held housing 10 to operatively link to the electric power arrangement 20 for providing different functions.

In particular, the multifunctional head unit comprises an inhaler unit 30 and a LED illumination unit 40 detachably and interchangeably coupled with the hand-held housing 10 to operatively link to the operation head 22.

As shown in FIG. 1, the inhaler unit 30 has a mouthpiece 31 and a treatment cavity 32 for receiving a treatment element therein. According to the preferred embodiment, the inhaler unit 30 comprises a tubular inhaling guider 33 longitudinally supported by the hand-held housing 10, wherein the inhaling guider 33 has a free end defining the mouthpiece 31 thereat and a detachable end defining the treatment cavity 32 thereat. The detachable end of the inhaler unit 30 is detachably coupled with the operation head 22 to detachably support the inhaler unit 30 at the hand-held housing 10.

When the inhaler unit 30 is operatively coupled with the operation head 22 of the electric power arrangement 20, the operation head 22 forms a heating head for heating the treatment element in the treatment cavity 32 so as to extract the treatment element for inhalation of an ingredient thereof via the mouthpiece 31.

As shown in FIG. 2, the LED illumination unit 40 comprises a LED light casing 41 detachably coupling with the operation head 22 and a LED light source 42 received in the LED light casing 41. When the LED illumination unit 40 is operatively coupled with the operation head 22 of the electric power arrangement 20, the operation head 22 forms an electrical adapter to electrically link the LED illumination unit 40 with the electric power source 42 for generating illumination light.

According to the preferred embodiment, the electric power source 21 comprises one or more rechargeable batteries 211 received in a battery compartment 212 in the hand-held housing 10 and a charging outlet 213 provided at the outer wall 11 of the hand-held housing 10 at the bottom face thereof for charging the rechargeable batteries 211 via AC power. Alternatively, the electric power source 21 can be the replaceable batteries that the rechargeable batteries 211 are replaced by the replaceable batteries in the battery compartment 212.

As shown in FIGS. 1 and 2, the electric power arrangement 20 further comprises a control circuit 23 controllably linked between the operation head 22 and the electric power source 21 and an automatic switch 24 which is provided at the operation head 22 and is controlled by the control circuit 23 to selectively switch an operation between the inhaler unit 30 and the LED illumination unit 40.

According to the preferred embodiment, the control circuit 23 is a circuit supported in the hand-held housing 10, wherein the control circuit 23 has a first control circuit configuration to control the operation of the operation head 22 as the heating head for the inhaler unit 30 and a second control circuit configuration to control the operation of the operation head 22 as the electric adapter for the LED illumination unit 40. Accordingly, the first control circuit configuration is a heating control configuration while the second control circuit configuration is a light control configuration.

The control circuit 23 further has a charging protection circuit configuration linked to the electric power source 21 for preventing the short circuit of the control circuit 23 and the over-charging of the electric power source 21. It is worth mentioning that the electric power source 21 can be re-charged over 800 times.

In addition, the electric power arrangement 20 further comprises a display panel 27 provided at one of the side faces of the outer wall 11 of the hand-held housing 10 as shown in FIG. 3, wherein the display panel 27 has a plurality of light indicators electrically linked to the control circuit 23 for indicating the status of the LED torch. For example, one of the light indicators will be flashed when the electric power source 21 is charging to indicate the charging status of the electric power source 21. One of the light indicators will be flashed to indicate the electrical power level of the electric power source 21. One of the light indicators will be flashed to indicate the operation status, such as on-and-off status of the electric power arrangement 20.

The automatic switch 24 is embodied as an auto detector for detecting the connection of the operation head 22 with respect to one of the inhaler unit 30 and the LED illumination unit 40. In particular, the automatic switch 24 is operatively linked to the first and second circuit configurations of the control circuit 23, such that when the inhaler unit 30 is coupled at the operation head 22, the first control circuit configuration of the control circuit 23 is activated while the second control circuit configuration of the control circuit 23 is deactivated. Likewise, when the LED illumination unit 40 is coupled at the operation head 22, the first control circuit configuration of the control circuit 23 is deactivated while the second control circuit configuration of the control circuit 23 is activated.

Preferably, the automatic switch 24 comprises a magnetic sensor switch 241 provided at the operation head 22 and a magnetic element 242 only provided at the inhaler unit 30 at the detachable end thereof. Therefore, when the inhaler unit 30 is detachably coupled with the operation head 22, the magnetic sensor switch 241 is switched on by detecting a presence of magnetic field via the magnetic element 242, such that the control circuit 23 automatically configures the operation head 22 as the heating head for heating up the treatment element by activating the first control circuit configuration only.

When the LED illumination unit 40 is detachably coupled with the operation head 22, the magnetic sensor switch 241 is switched off by detecting no magnetic field at the LED illumination unit 40, such that the control circuit 23 automatically configures the operation head 22 as the electrical adapter to electrically connect with the LED illumination unit 40 by activating the second control circuit configuration only.

It is appreciated that other detecting switches can be used for detecting the connection of the operation head 22 with respect to one of the inhaler unit 30 and the LED illumination unit 40 in order to activate one of the first and second control circuit configurations.

According to the preferred embodiment, the operation head 22 comprises a heater head socket 221 detachably coupling with the inhaler unit 30 and a light head socket 222 which is positioned adjacent to the heater head socket 221 to detachably couple with the LED illumination unit 40. Accordingly, the heater head socket 221 and the light head socket 222 are operatively linked to the first and second control circuit configurations of the control circuit 23 respectively.

As shown in FIG. 1, the heater head socket 221 is positioned at the front face of the outer wall 11 of the hand-held housing 10, wherein a heating element 223 is controllably linked with the control circuit 23 and is positioned behind the heater head socket 221 for heat generation. Accordingly, the heating element 223 can be ceramic, silicon, or metal adapted for heat generation. It is worth mentioning that the heating temperature of the heating element 223 can be precisely controlled by the control circuit 23 by controlling the current passing therethrough. It is appreciated that using other electronic components such as capacitors, resistors, or the like can precisely control the heating temperature of the heating element 223.

The heater head socket 221 is made of heat conductive material and is arranged in such a manner that when the heating element 223 is electrically activated by the control circuit 23, i.e. the activation of the first control circuit configuration, the heater head socket 221 will form the heating head for heat generation. The heating temperature of the heating element 223 can be adjusted as high as 200° C. while the heating temperature of the heater head socket 221 can be adjusted as high as 50 to 60° C. Therefore, when the detachable end of the inhaler unit 30 is coupled at the heater head socket 221, the heat from the heater head socket 221 will transmit to the treatment cavity 32 to as to extract the treatment element therein for inhalation of an ingredient thereof via the mouthpiece 31. It is worth mentioning that the treatment cavity 32 is formed at the detachable end of the inhaler unit 30 and is made of heat conductive material for effectively conducting heat from the heater head socket 221.

Accordingly, the LED torch of the present invention further comprises a PTC temperature sensor operatively linked to the control circuit 23 to detect the heating temperature of the heating element 223, wherein the PTC temperature sensor is adapted for avoiding the overheating of the heater head socket 221 and burning the treatment element within the treatment cavity 32 by the heat from the heater head socket 221.

According to the preferred embodiment, the hand-held housing 11 has a plurality of air vents 12 provided at the outer side thereof adjacent to the operation head 22 for heat dissipation. In particular, the air vents 12 are a plurality of through slots formed at the top portion of the hand-held housing 11 adjacent to the location of the heater head socket 221 for heat dissipation.

Figure 5:
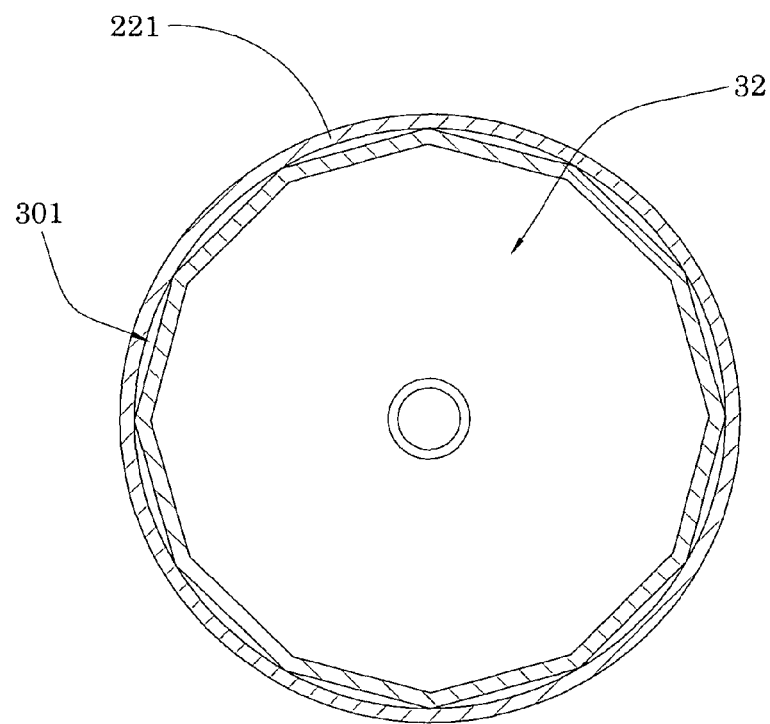
FIG. 5 illustrates a clearance between the heater head socket and the inhaler unit according to the above preferred embodiment of the present invention.

As shown in FIG. 5, the heater head socket 221 has a circular cross section while the detachable end of the inhaler unit 30, i.e. the treatment cavity 32, has a polygonal cross section. Therefore, when the detachable end of the inhaler unit 30 is detachably coupled with the heater head socket 221, a clearance 301 is formed between an inner surface of the heater head socket 221 and an outer surface of the detachable end of the inhaler unit 30 for air circulation. In other words, during the inhalation of the ingredient of the treatment element via the mouthpiece 31, air (oxygen) can pass through the clearance 301 into the treatment cavity 32 for enhancing the extraction of the treatment element.

As shown in FIG. 2, the light head socket 222 is positioned at the front face of the outer wall 11 of the hand-held housing 10 at the position below the heater head socket 221, wherein the light head socket 222 forms the electrical adapter to electrically link the LED illumination unit 40 with the electric power source 42. The LED illumination unit 40 further comprises an electrical terminal 43 rearwardly extended from the LED light casing 41 and electrically linked to the LED light source 42, wherein the electrical terminal 43 is detachably coupled with the light head socket 222 to electrically link the LED light source 42 with the electric power arrangement 20. The LED illumination unit 40 further comprises a retention head 44 rearwardly extended from the LED light casing 41 to align with the heater head socket 221, wherein when the electrical terminal 43 is detachably coupled with the light head socket 222, the retention head 44 is detachably coupled with the heater head socket 221 to retain the LED illumination unit 40 in position. It is worth mentioning that when the electrical terminal 43 is detachably coupled with the light head socket 222, the first control circuit configuration of the control circuit 23 is deactivated. Therefore, the heater head socket 221 will not generate heat. Thus, the heater head socket 221 forms a retention member to detachably couple with the retention head 44 to hold the LED illumination unit 40 in position. In addition, when the detachable end of the inhaler unit 30 is detachably coupled with the heater head socket 221, the bottom portion of the detachable end of the inhaler unit 30 will cover up the light head socket 222.

As shown in FIGS. 1 to 4, the electric power arrangement 20 further comprises an operation actuator 25 and a safety actuator 26 spacedly provided at the outer wall 11 of the hand-held housing 10 to operatively linked to the control circuit 23. Accordingly, the operation actuator 25 and the safety actuator 26 are provided at the front and rear faces of the outer wall 11 of the hand-held housing 10. The operation actuator 25 and the safety actuator 26 must be actuated at the same time in order to start operating the electric power arrangement.

According the operation of the LED torch of the present invention is illustrated as follows.

For connection of the inhaler unit 30, the user is able to fill the treatment element in the treatment cavity 32. The detachable end of the inhaler unit 30 can be detachably coupled with the heater head socket 221 of the operation head 22. Then, the user must press the operation actuator 25 and the safety actuator 26 at the same time for a predetermined time, such as 2 seconds, in order to switch on the electric power arrangement 20 at the standby mode. Once the detachable end of the inhaler unit 30 is detachably coupled with the heater head socket 221, the operation actuator 25 can be pressed to start the heat generation from the heater head socket 221. It is worth mentioning that when the inhaler unit 30 is detachably coupled with the heater head socket 221, the magnetic sensor switch 241 is switched on by detecting a presence of magnetic field via the magnetic element 242, such that the control circuit 23 automatically configures the heater head socket 221 as the heating head for heating up the treatment element by activating the first control circuit configuration only. Accordingly, the heating temperature will reach 200° C. for about one minute. In addition, the fully charged electrical power from the electric power source 21 can provide 5 hours of heating operation of the heater head socket 221 for the inhaler unit 30. In order to stop the operation of the heater head socket 221, the user is able to press the operation actuator 25 again so as to deactivate the first control circuit configuration for stop generating heat. It is worth mentioning that the control circuit 23 will also stop the operation of the heater head socket 221 after a predetermined of continuous using time, such as 20 minutes, for preventing the overheating of the operation head 22. The user is able to press the safety actuator 26 once in order to switch off the electric power arrangement 20 of the LED torch from the standby mode to an off mode.

It is worth mentioning that the heat from the operation head 22 is powered by the electric power source 21 instead of conventional piezoelectric igniter powered by combustible fuel, i.e. butane gas. Therefore, the user does not have to refill the butane gas once the butane gas is used up or have to carry additional butane gas bottle for refilling purpose. In other words, no leakage of the combustible fuel will be occurred in the present invention. In particular, once the operation actuator 25 is pressed twice to deactivate the first control circuit configuration for stop generating heat, no residual butane gas is left in the hand-held housing 10, such that the user will not inhale any butane gas before and after the operation of the LED torch of the present invention. On the other hand, the LED torch has no air pollution due to the absence of the butane gas. When the electrical power level of the electric power source 21 is low, the user is able to recharge the rechargeable battery as the electric power source 21 by electrically plugging the electric power source 21 to the AC outlet via the charging outlet 213 or replacing the replaceable battery as the electric power source 21.

For connection of the LED illumination unit 40, the user is able to detachably couple the LED illumination unit 40 with the light head socket 222 of the operation head 22. Then, the user must press the operation actuator 25 and the safety actuator 26 at the same time for a predetermined time, such as 2 seconds, in order to switch on the electric power arrangement 20 at the standby mode. Once the LED illumination unit 40 is detachably coupled with the light head socket 222, the operation actuator 25 can be pressed to switch on the LED light source 42. The fully charged electrical power from the electric power source 21 can provide 15 hours of illumination operation for the LED illumination unit 40. It is worth mentioning that the LED illumination unit 40 will generate light for illumination when the operation actuator 25 is pressed once. The illumination unit 40 will generate light with flash manner when the operation actuator 25 is pressed twice. The illumination 40 will be switched off when the operation actuator 25 is pressed at the third time. Likewise, the user is able to press the safety actuator 26 once in order to switch off the electric power arrangement 20 of the LED torch from the standby mode to the off mode.

It is appreciated that the LED illumination unit 40 can be replaced by other electrical devices powered by the electric power arrangement 20.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An LED torch, comprising:
a hand-held housing;
an electric power arrangement which comprises an electric power source received in said hand-held housing and an electrical-powered operation head which is electrically linked to said electric power source and is located at an outer wall of said hand-held housing; and
a multifunctional head unit which comprises an inhaler unit and an LED illumination unit detachably and interchangeably coupled with said hand-held housing to operatively link to said operation head, wherein said inhaler unit has a mouthpiece and a treatment cavity for receiving a treatment element therein, wherein when said inhaler unit is operatively coupled with said operation head of said electric power arrangement, said operation head forms a heating head for heating said treatment element in said treatment cavity so as to extract said treatment element for inhalation of an ingredient thereof via said mouthpiece, wherein when said LED illumination unit is operatively coupled with said operation head of said electric power arrangement, said operation head forms an electrical adapter to electrically link said LED illumination unit with said electric power source for generating illumination light, wherein said electric power arrangement further comprises a control circuit controllably linked between said operation head and said electric power source, and an automatic switch which is provided at said operation head and is controlled by said control circuit to selectively switch an operation between said inhaler unit and said LED illumination, wherein said automatic switch comprises a magnetic sensor switch provided at said operation head and a magnetic element provided at said inhaler unit, wherein when said inhaler unit is detachably coupled with said operation head, said magnetic sensor switch is switched on by detecting a presence of magnetic field via said magnetic element, such that said control circuit automatically configures said operation head as said heating head for heating up said treatment element, wherein when said LED illumination unit is detachably coupled with said operation head, said magnetic sensor switch is switched off by detecting no magnetic field at said LED illumination unit, such that said control circuit automatically configures said operation head as said electrical adapter to electrically connect with said LED illumination unit.

2. The LED torch, as recited in claim 1, wherein said operation head comprises a heater head socket detachably coupling with said inhaler unit and a light head socket which is positioned adjacent to said heater head socket to detachably couple with said LED illumination unit.

3. The LED torch, as recited in claim 2, wherein said control circuit controllably linked to said heater head socket and said light head socket, and is arranged to controllably disable one of said heater head socket and said light head socket in response to said automatic switch.

4. The LED torch, as recited in claim 3, wherein said heater head socket has a circular cross section, wherein a detachable end of said inhaler unit has a polygonal cross section, such that when said detachable end of said inhaler unit is detachably coupled with said heater head socket, a clearance is formed between an inner surface of said heater head socket and an outer surface of said detachable end of said inhaler unit for air circulation.

5. The LED torch, as recited in claim 4, wherein said electric power arrangement further comprises an operation actuator and a safety actuator spacedly provided at said outer wall of said hand-held housing to operatively link to said control circuit and arranged in such a manner that said operation actuator and said safety actuator must be actuated at the same time in order to start operating said electric power arrangement.

6. The LED torch, as recited in claim 5, wherein said electric power source comprises one or more rechargeable batteries received in said hand-held housing and a charging outlet provided at said outer wall of said hand-held housing for charging said rechargeable batteries via AC power.

7. The LED torch, as recited in claim 6, wherein said hand-held housing has a plurality of air vents provided at said outer side thereof adjacent to said operation head for heat dissipation.

8. The LED torch, as recited in claim 5, wherein said electric power source comprises a battery compartment received in said hand-held housing for receiving one or more replaceable batteries.

9. The LED torch, as recited in claim 8, wherein said hand-held housing has a plurality of air vents provided at said outer side thereof adjacent to said operation head for heat dissipation.

10. The LED torch, as recited in claim 3, wherein said electric power arrangement further comprises an operation actuator and a safety actuator spacedly provided at said outer wall of said hand-held housing to operatively link to said control circuit and arranged in such a manner that said operation actuator and said safety actuator must be actuated at the same time in order to start operating said electric power arrangement.

11. The LED torch, as recited in claim 3, wherein said electric power source comprises one or more rechargeable batteries received in said hand-held housing and a charging outlet provided at said outer wall of said hand-held housing for charging said rechargeable batteries via AC power.

12. The LED torch, as recited in claim 3, wherein said electric power source comprises a battery compartment received in said hand-held housing for receiving one or more replaceable batteries.

13. The LED torch, as recited in claim 2, wherein said heater head socket has a circular cross section, wherein a detachable end of said inhaler unit has a polygonal cross section, such that when said detachable end of said inhaler unit is detachably coupled with said heater head socket, a clearance is formed between an inner surface of said heater head socket and an outer surface of said detachable end of said inhaler unit for air circulation.

14. An LED torch, comprising:
a hand-held housing;
an electric power arrangement which comprises an electric power source received in said hand-held housing and an electrical-powered operation head which is electrically linked to said electric power source and is located at an outer wall of said hand-held housing; and
a multifunctional head unit which comprises an inhaler unit and an LED illumination unit detachably and interchangeably coupled with said hand-held housing to operatively link to said operation head, wherein said inhaler unit has a mouthpiece and a treatment cavity for receiving a treatment element therein, wherein when said inhaler unit is operatively coupled with said operation head of said electric power arrangement, said operation head forms a heating head for heating said treatment element in said treatment cavity so as to extract said treatment element for inhalation of an ingredient thereof via said mouthpiece, wherein when said LED illumination unit is operatively coupled with said operation head of said electric power arrangement, said operation head forms an electrical adapter to electrically link said LED illumination unit with said electric power source for generating illumination light, wherein said operation head comprises a heater head socket detachably coupling with said inhaler unit and a light head socket which is positioned adjacent to said heater head socket to detachably couple with said LED illumination unit.

15. An LED torch, comprising:
a hand-held housing;
an electric power arrangement which comprises an electric power source received in said hand-held housing and an electrical-powered operation head which is electrically linked to said electric power source and is located at an outer wall of said hand-held housing; and
a multifunctional head unit which comprises an inhaler unit and an LED illumination unit detachably and interchangeably coupled with said hand-held housing to operatively link to said operation head, wherein said inhaler unit has a mouthpiece and a treatment cavity for receiving a treatment element therein, wherein when said inhaler unit is operatively coupled with said operation head of said electric power arrangement, said operation head forms a heating head for heating said treatment element in said treatment cavity so as to extract said treatment element for inhalation of an ingredient thereof via said mouthpiece, wherein when said LED illumination unit is operatively coupled with said operation head of said electric power arrangement, said operation head forms an electrical adapter to electrically link said LED illumination unit with said electric power source for generating illumination light, wherein said electric power arrangement further comprises a control circuit controllably linked between said operation head and said electric power source, and an automatic switch which is provided at said operation head and is controlled by said control circuit to selectively switch an operation between said inhaler unit and said LED illumination, wherein said operation head comprises a heater head socket detachably coupling with said inhaler unit and a light head socket which is positioned adjacent to said heater head socket to detachably couple with said LED illumination unit.

16. The LED torch, as recited in claim 15, wherein said control circuit controllably linked to said heater head socket and said light head socket, and is arranged to controllably disable one of said heater head socket and said light head socket in response to said automatic switch.

17. An LED torch, comprising:
a hand-held housing;
an electric power arrangement which comprises an electric power source received in said hand-held housing and an electrical-powered operation head which is electrically linked to said electric power source and is located at an outer wall of said hand-held housing; and
a multifunctional head unit which comprises an inhaler unit and an LED illumination unit detachably and interchangeably coupled with said hand-held housing to operatively link to said operation head, wherein said inhaler unit has a mouthpiece and a treatment cavity for receiving a treatment element therein, wherein when said inhaler unit is operatively coupled with said operation head of said electric power arrangement, said operation head forms a heating head for heating said treatment element in said treatment cavity so as to extract said treatment element for inhalation of an ingredient thereof via said mouthpiece, wherein when said LED illumination unit is operatively coupled with said operation head of said electric power arrangement, said operation head forms an electrical adapter to electrically link said LED illumination unit with said electric power source for generating illumination light, wherein said electric power arrangement further comprises a control circuit controllably linked between said operation head and said electric power source, and an automatic switch which is provided at said operation head and is controlled by said control circuit to selectively switch an operation between said inhaler unit and said LED illumination, wherein said electric power arrangement further comprises an operation actuator and a safety actuator spacedly provided at said outer wall of said hand-held housing to operatively link to said control circuit and arranged in such a manner that said operation actuator and said safety actuator must be actuated at the same time in order to start operating said electric power arrangement.

\* \* \* \* \*